United States Patent [19]

Lauwerys et al.

[11] 4,329,152

[45] May 11, 1982

[54] DETERMINATION OF $\beta_2$-MICROGLOBULIN IN HUMAN URINE AND SERUM BY LATEX IMMUNOASSAY

[75] Inventors: Robert R. Lauwerys, Tervuren; Alfred M. Bernard, Brussels, both of Belgium

[73] Assignee: International Lead Zinc Research Organization, Inc., New York, N.Y.

[21] Appl. No.: 194,268

[22] Filed: Oct. 6, 1980

[51] Int. Cl.³ .................... G01N 33/54; G01N 35/02
[52] U.S. Cl. .................... 23/230 B; 422/64; 422/73; 424/12
[58] Field of Search .............. 23/230 B; 424/12; 422/64, 73

[56] References Cited

U.S. PATENT DOCUMENTS 4,162,895 7/1979 Cambiaso .................... 23/230 B X

OTHER PUBLICATIONS

C. L. Cambiaso et al., Journal of Immunological Methods, 18, 33–44 (1977).
J. Shuster et al., Clinica Chimica Acta, 67, 307–313 (1976).

Primary Examiner—Sidney Marantz
Attorney, Agent, or Firm—Brumbaugh, Graves, Donohue & Raymond

[57] ABSTRACT

A highly sensitive method has been developed for the determination of $\beta_2$-microglobulin in human urine or serum samples. This method is based on the agglutination of $\beta_2$-microglobulin by latex particles coated with an anti-body against $\beta_2$-microglobulin in a stabilizing solution.

4 Claims, 7 Drawing Figures and  # DETERMINATION OF $\beta_2$-MICROGLOBULIN IN HUMAN URINE AND SERUM BY LATEX IMMUNOASSAY

BACKGROUND OF THE INVENTION $\beta_2$-microglobulin ($\beta_2$-m) is a low molecular weight protein (mol. wt. 11,800) present in small amounts in normal urine and other biological fluids. $\beta_2$-m is structurally related to immunoglobulin G and to the cell-surface histo-compatibility antigens. It is synthetized by all nucleated cells and is present on their surface. The biological role of $\beta_2$-m is still unknown.

In healthy subjects, the concentration of $\beta_2$-m in serum fluctuates within a narrow range of values, from 0.09 to 0.24 mg/100 ml. Elevated serum levels are found in malignant disorders, particularly in multiple myeloma and monocytic leukemia, and in patients with decreased glomerular filtration rate. In the latter case, the serum $\beta_2$-m is considered as a very sensitive index of impaired glomerular filtration rate. In healthy subjects, the amount of $\beta_2$-m excreted in urine is small (70–80 $\mu$g/24 hr.). The urinary excretion of $\beta_2$-m is considerably increased in case of tubular dysfunction as observed in chronic cadmium poisoning, Fanconi's syndrome, Balkan nephropathy and Wilson's disease. In occupational medicine, the determination of $\beta_2$-m in urine is regarded as the most sensitive test for detecting at an early stage a tubular damage induced by excessive exposure to cadmium.

Determination of $\beta_2$-m in human urine or serum was initially performed by single radial immunodiffusion. This method is, however, not sensitive enough for detecting $\beta_2$-m in normal urine without a preliminary concentration step. Radioimmunoassay (R.I.A.) methods were then developed which can accurately measure $\beta_2$-m concentrations in normal urine or serum without a preconcentration of the samples. The two available R.I.A. methods for $\beta_2$-m analysis are the solid phase R.I.A. of Evrin et al. "Radioimmunoassay of $\beta_2$-microglobulin in human biological fluids," Scand. J. Clin. Lab. Invest. 28, 439–443 (1971) and the double antibody method of Shuster et al. "$\beta_2$-microglobulin in neoplastic diseases," Clin. Chim. Acta 67, 307–313 (1976). Solid phase R.I.A. has been commercialized by Pharmacia Diagnostic A.B. (Phadebas ®, $\beta_2$-micro Test, Uppsala, Sweden). The disadvantages of the radioisotopic methods (short shelf life of the reagents, high cost of the kits, health hazards, time consuming technique) have lead us to develop an alternative method more convenient for routine evaluation of $\beta_2$-m.

A lymphocytotoxicity inhibition technique for determining $\beta_2$-m has recently been proposed but this method is much less accurate and sensitive than R.I.A. and can give only a rough estimate of the $\beta_2$-m level. According to the present invention, we propose a new highly sensitive method which does not require the use of radioisotopes. This method called latex immunoassay offers at least the same precision, specificity and sensitivity as the R.I.A., but presents the advantage of being much more simple and rapid.

BRIEF SUMMARY OF THE INVENTION

A highly sensitive method has been developed for the determination of $\beta_2$-microglobulin ($\beta_2$-m) in human urine or serum. The method called latex immunoassay is based on the direct agglutination by $\beta_2$-m of latex particles coated by adsorption with an antibody against $\beta_2$-m. The agglutination is quantified by counting the remaining unagglutinated particles or by turbidimetry. The assayable concentration range is 1–32 $\mu$g/l with a detection limit of 0.5 $\mu$g/l. The within-assay coefficient of variation (CV) based on 10 determinations of $\beta_2$-m in urine and serum at 2 different dilutions range from 4.6 to 8.7 percent. The between assay CV, calculated from 10 determinations of $\beta_2$-m in urine and serum, are 10 and 8.4 percent respectively.

Recovery of $\beta_2$-m in urine is on the average 97 percent and in serum 104 percent (n=10). No urine or serum component was found to interfere with the assay. The correlations between values of $\beta_2$-m in urine or serum obtained by radioimmunoassay and latex immunoassay are excellent. The average $\beta_2$-m concentrations in serum and urine from 33 healthy male subjects (aged 20 to 67 years) are 0.15 mg/100 ml and 54 $\mu$g/g creatinine respectively.

BRIEF DESCRIPTION OF THE DRAWINGS

The foregoing and other features of the present invention will be more readily apparent from the following detailed description and drawings in which.

DESCRIPTION OF THE PREFERRED EMBODIMENTS

For several years, qualitative agglutination tests using latex particles have been used for the diagnosis of rhumatoid arthritis, pregnancy, viral or bacterial infections and other diseases. Recently, in order to develop quantitative assays based on latex agglutination, several reading procedures like nephelometry, turbidimetry and particle counting have been proposed. With the latter technique, Cambiaso et al. "Particle counting immunoassay (PACIA). I. A general method for the determination of antibodies, antigens and haptens," J. Imm. Meth. 18, 33–44 (1977) have shown that, due to their high sensitivity, latex agglutination tests could be applied in areas so far restricted to R.I.A. The latex immunoassay (L.I.A.) method according to the present invention has a specificity, a sensitivity and a precision quite comparable to R.I.A., but this new method has the advantage that it does not require any labelled reagents. Many disadvantages associated with the use of radioisotopes (shelf life, health hazards, etc.) are thus eliminated.

Figure 4:
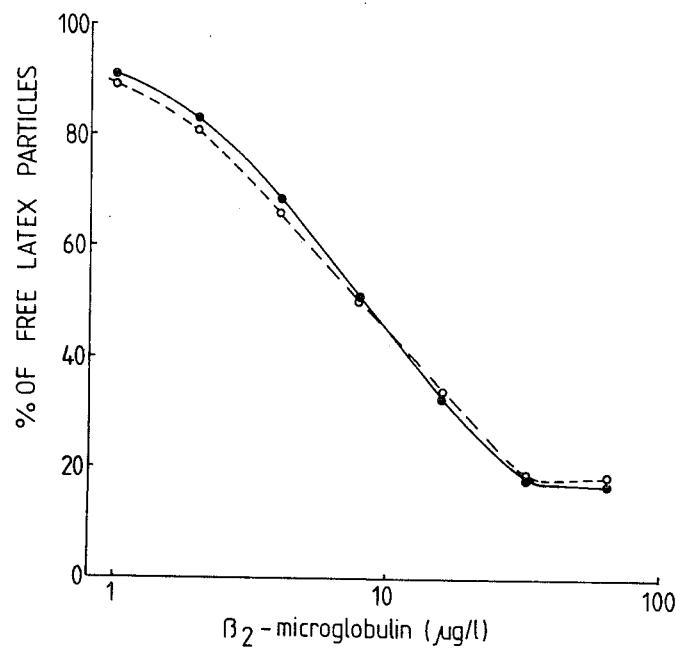
FIG. 4 shows agglutination curves obtained with serial dilutions in GBS-BSA buffer or purified $\beta_2$-m (•-•), pooled urines (o--o), pooled sera (Δ. . . Δ) and a serum with rhumatoid factor (□-.-□) respectively. The dilution ranges were for urine, $\frac{1}{2}$-1/256 and for serum 1/20–1/2560. The latex coated with anti-$\beta_2$-m was diluted 5 times before assay (lecture by particle counting).

Another advantage of L.I.A. is its simplicity. Latex particles are coated by simple mixing with the antibody in less than 2 hours and the preparation obtained can be stored at 4° C. for months before use. The assay itself is particularly rapid since it consists in an incubation of 15 to 30 minutes followed directly by the reading. The complete determination of $\beta_2$-m (including dilution of samples, incubation and reading) in 20 unknown samples can be performed manually within 3 hours. Furthermore, the consumption of reagents is insignificant since 5 $\mu$l (78.5 $\mu$g) of DAKO antibody and 50 $\mu$l of latex (10 percent suspension) are sufficient for about one hundred analyses of $\beta_2$-m in duplicate (with a 10-fold dilution of the latex before assay). As shown in FIG. 4, no purified antigen is needed. A standard curve can be made from a reference serum with a known concentration of $\beta_2$-m. Reading can be performed with a particle counter or by turbidimetry with a photometer. The latter instrument is commonly found in clinical chemistry laboratories. Only the former method of measurement has been automatized in our laboratory, but no doubt that the second procedure can also be automatized. L.I.A. thus appears as a method of choice for the routine determination of $\beta_2$-m. This method is now currently applied in the laboratory as a screening test of tubular dysfunction in workers occupationally exposed to cadmium.

It is important to realize that the sensitivity, accuracy and precision achieved with the present L.I.A. method requires optimization of several parameters. The optimal assay conditions must be defined for each antigen-antibody system and from experience, it appears that, once the incubation conditions have been defined (temperature, agitation), essentially 4 parameters have to be optimized. The first one is the charge of latex particles in antibody. The charge required to obtain an agglutination curve in a range of antigen concentrations, depends on the titer and the avidity of the antiserum used. Latex particles coated with an antibody are unstable and agglutinate spontaneously due to interaction between Ig molecules. This aspecific agglutination can be suppressed by a subsequent coating of the latex particles with albumin which has a high affinity for latex. This is realized by diluting the latex particles (after desaggregation by shaking on a vortex) just before the assay with a stabilization solution containing bovine serum albumin. The pH of this solution, which is the second parameter to optimize, has to be adjusted so that interactions between Ig molecules are prevented by electrostatic repulsion of the negatively charged molecules of albumin. The higher the pH, the stronger will be this repulsion. The optimal pH will of course vary with the charge of latex in antibody (which is a function of the quality of the antiserum) as well as with the characteristics and hence the source of the antibody.

For $\beta_2$-m L.I.A. the stability of coated latex particles is the best when the pH of the stabilization solution is equal to 10. Above this pH value, the specific agglutination decreases progressively. Ten is thus the optimal pH value giving the maximum specific agglutination with the minimum aspecific one.

The degree of stabilization of the latex particles can be estimated by calculating the percentage of aspecific agglutination occurring in the zero standards during incubation. Aspecific agglutination was estimated by measuring the decrease in the optical density (OD) at 360 nm of the zero standard. Reproducible results will be obtained only if aspecific agglutination does not exceed about 10 percent during incubation. Under these conditions, the latex suspension is stable during pipetting. Within 20 minutes (the time required to pipet a standard curve and about 20 unknown samples), no significant agglutination occurs in the latex suspension.

Figure 2:
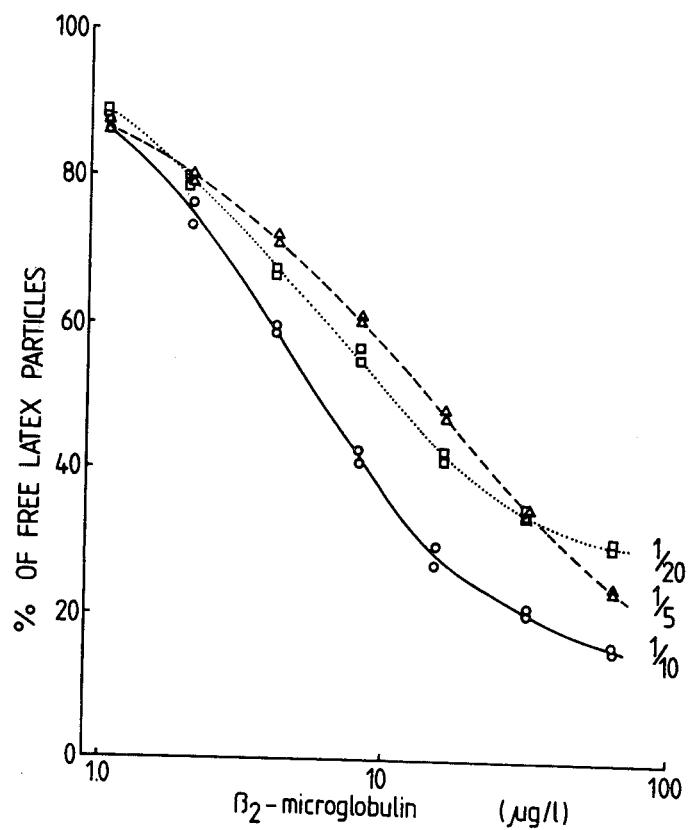
FIG. 2 shows standard curves of $\beta_2$-m obtained with anti-$\beta_2$-m coated latex particles diluted 5, 10, or 20-times in the stabilization buffer before assay (lecture by particle counting).

The third parameter to be optimized is the concentration of free latex particles in the incubation mixture. As illustrated in FIG. 2, once the latex particles are stabilized, there is an optimal dilution rate of the latex before assay. Finally, depending on the degree of stability of the latex and on the incubation conditions (temperature and agitation), the time required for optimal agglutination may vary and must also be determined. It is essential to keep in mind that all these parameters are interdependent. For instance, increasing the charge of latex in antibody will affect its stability and hence the concentration of free latex particles during incubation.

Postzone phenomenon with excess antigen are observed with antibody-coated latex as with a free antibody. The level of $\beta_2$-m at which a postzone appears is proportional to the charge of antibodies on latex particles and to the concentration of latex particles in the incubation mixture. When latex particles are diluted 5 times before assay instead of 10 times, postzone is observed at a concentration of $\beta_2$-m about twice as high (around 100 mg/l). Inversely, when the concentration of free latex particles is reduced by aspecific agglutination, postzone occurs earlier.

The setting of the optimal conditions may appear laborious. However, when they have been defined for one protein and one batch of antibody, no reevaluation is required for several years since the amount of antibody used in L.I.A. procedure is extremely small.

In accordance with the invention, the following description of specific test procedures is illustrative:

PURIFICATION OF $\beta_2$-m

Urine from a cadmium-exposed worker with tubular lesions was 100-times concentrated by pressure dialysis through a PM-10 membrane. The concentrate was chromatographed on a column of Sephadex ® G-75 Superfine in 0.05 mol/l Tris-HCl buffer pH 7.4 containing 0.2 mol/l NaCl and 0.02 g/l NaN$_3$. The fractions containing $\beta_2$-m were pooled and equilibrated with 0.01 mol/l Tris-HCl buffer pH 7.9 containing 0.02 mol/l NaCl. $\beta_2$-m was then purified by DEAE-cellulose chromatography with a linear NaCl gradient from 0.02 to 0.2 mol/l in 0.01 mol/l Tris-HCl buffer. This $\beta_2$-m preparation was lyophylized and stored at $-18°$ C. $\beta_2$-m was found to be pure by agarose and polyacrylamide gel electrophoresis and by Ouchterlony double immunodiffusion against an anti-retinol binding protein serum. The concentration of $\beta_2$-m was estimated by using a molar extinction coefficient of 19,850.

ANTIBODIES

Rabbit immunoglobulins against human $\beta_2$-m were obtained from Dako Immunoglobulin (Lot No. 039 B, Copenhagen, Denmark). The Ig concentration estimated by reading the optical density ($E_{280\,nm} = 13.8$) was 15.7 mg/ml. The antiserum against retinol binding protein was from Behringwerke A. G., Marburg/Lahn, West Germany.

LATEX PARTICLES

Polystyrene latex particles, 0.79 μm diameter (ESTAPOR K 109) were employed as a 10 percent suspension.

ASSAY BUFFER

Glycine buffer saline (GBS) was used throughout the latex immunoassay. This buffer was prepared by a 10-fold dilution of a stock buffer containing 1 mol/l glycine, 1.7 mol/l NaCl, 0.076 mol/l NaN$_3$ and adjusted to pH 9 with NaOH (10 mol/l).

URINE AND SERUM SAMPLES

Urine and serum samples were collected from a group of 33 apparently healthy male subjects, aged from 20 to 67 years. Urine specimens were also obtained from 34 male workers with prolonged exposure to cadmium (20 years on the average). Serum with elevated levels of $\beta_2$-m were collected from 18 patients with decreased glomerular filtration rate. In order to prevent degradation of $\beta_2$-m, the urine samples were alkalinized by adding to 10 ml of urine 1 ml of a 0.4 mol/l KH$_2$PO$_4$/K$_2$HPO$_4$ buffer pH 7.6. All samples were stored at $-18°$ C. until $\beta_2$-m analysis.

LATEX IMMUNOASSAY

Coating of latex particles with the antibody

Five μl (78.5 μg) of rabbit immunoglobulin against $\beta_2$-m (DAKO) were diluted in 0.4 ml GBS. Fifty μl of the 10 percent latex suspension were then added under continuous agitation. After about 1 hour of incubation at ambient temperature, the latex particles were precipitated by centrifugation at 25,000 g for 10 minutes (25° C.) and washed twice in 1 ml GBS. Finally, they were redispersed in 1 ml GBS. Although the latex particles coated with Ig are unstable and agglutinate rapidly (within several hours), they can be stored at 4° C. for months before use, without significant decrease of their agglutinability by $\beta_2$-m.

Preparation of samples and standards

Dilutions of serum (or plasma) and urine samples and of purified $\beta_2$-m solutions were made in a GBS buffer containing 1 g/l of bovine serum albumin and adjusted to pH 9 (GBS-BSA buffer). Serum samples were routinely diluted 200 to 400 times and urine samples 10 to 20 times before assay.

Assay procedure

Twenty μl of $\beta_2$-m standard solution or of diluted urine or serum samples were pipetted in duplicate in glass test tubes. Tubes containing 20 μl of GBS-BSA buffer only (zero standard) were regularly spaced in each series of determination. Just before incubation, the latex particles coated with the antibody were stabilized as follows: the latex particles from the stock preparation were resuspended by gentle shaking and the adequate volume was transferred in a plastic tube with an internal diameter of about 1 cm. The tube was vigorously shaken (for 1-2 minutes) with a vortex in order to destroy the latex aggregates formed during storage. The latex was then immediately diluted (10 times ideally, see FIG. 2) in a stabilization solution. This solution was composed of a GBS buffer containing 10 g/l of BSA, carefully adjusted to pH 10 (at 25° C.) and filtered twice on a 0.45 μm Millipore filter. This stabilization solution must be either prepared freshly or stored frozen and thawed just before use. Fifty μl of the stabilized latex were then added to each test tube. The content of the tube was rapidly mixed and incubated for 15 to 30 minutes at 37° C. in a shaking water bath (70-80 cycles/minute, 5.5 cm amplitude). The incubation was stopped by adding 5 ml of GBS containing 1 ml/l of Tween 20. The latter solution was also filtered on a 0.45 μm Millipore filter before use. Finally, the tubes were stoppered and inverted 3 to 4 times to ensure homogenization of the latex suspension before lecture.

Measurement

Figure 1:
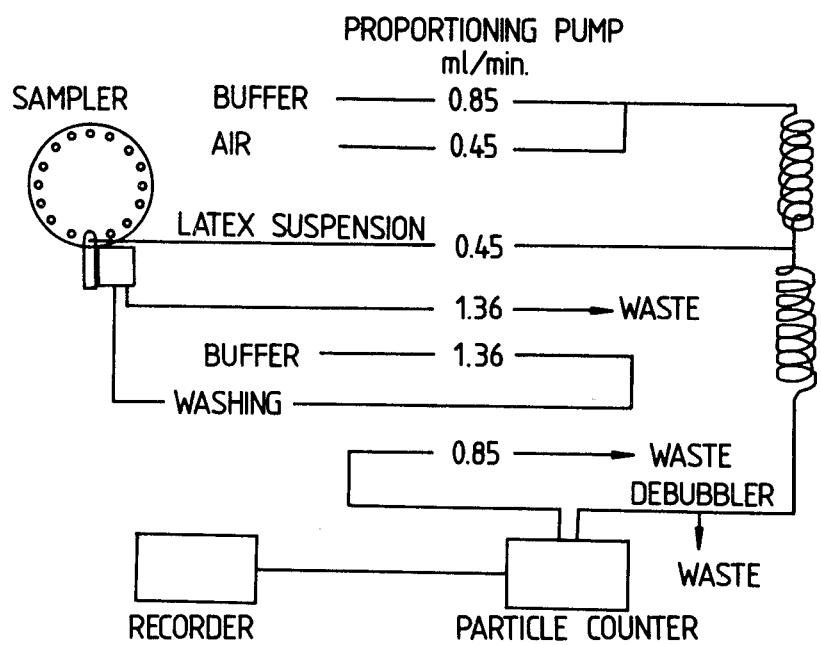
FIG. 1 is a flow diagram for automated reading of latex agglutination by particle counting.

The measurement was usually performed automatically as proposed by Cambiaso et al. "Particle counting immunoassay (PACIA). I. A general method for the determination of antibodies, antigens and haptens," J. Imm. Meth. 18, 33-44 (1977). The unagglutinated latex particles were counted by using a Technicon ® Autocounter equipped with a double threshold system. The latex suspension was aspirated with a Carlo Erba sampling system (FIG. 1). The sampler was run at 40/hour with a sample wash ratio of 1/1. The signal was recorded on a BD 9 Kipp and Zonen ® recorder with a continuously adjustable scale. The number of unagglutinated latex particles was expressed in percent of the total number of free particles obtained with the zero standard.

In some cases, the reading was made by turbidimetry. The optical density (OD) of the latex suspension was read in a 2 cm-cuvette at 360 nm (the maximum of absorbance) with Zeiss ® PMQ II spectrophotometer. The agglutination was then expressed as the difference between the OD of the zero standard and that of the latex incubated with $\beta_2$-m.

Other methods

Radioimmunoassay of $\beta_2$-m was performed by using the Phadebas ® $\beta_2$-micro Test. The range of the standard curve was 3-96 μg $\beta_2$-m/l. The lowest dilution rate recommended by the suppliers being 5 times, 15 μg $\beta_2$-m/l is the lowest $\beta_2$-m concentration in urine which can accurately be measured with the Phadebas ® $\beta_2$-micro Test. Samples of pooled sera or urines were chromatographed on a column (70×1.6 cm) of Superfine Sephadex ® G-75 equilibrated with a 0.05 mol/l Tris-HCl buffer pH 7.4 containing 0.2 mol/l NaCl and 0.02 g/l NaN$_3$.

RESULTS

Standard Curves of Purified $\beta_2$-m

Figure 3:
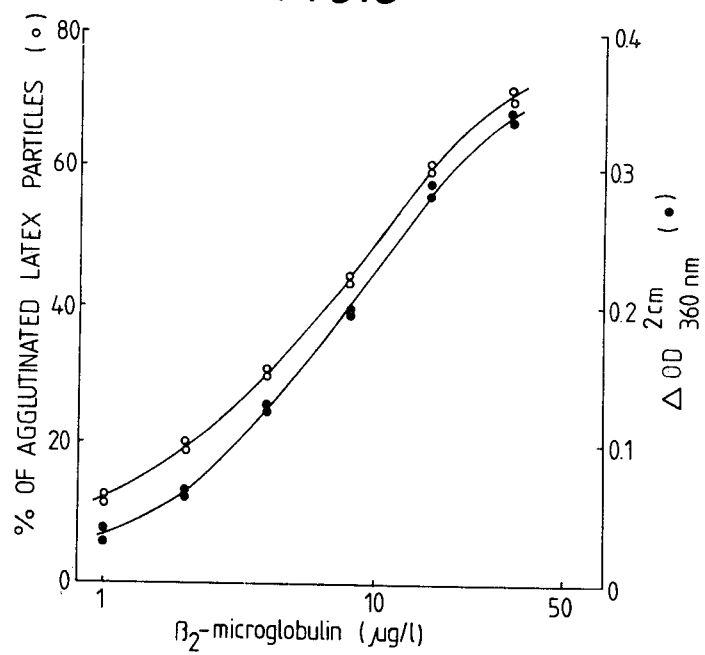
FIG. 3 shows a standard curve of $\beta_2$-m read by counting the remaining unagglutinated latex particles (°) or by determining the decrease of optical density at 360 nm. (•)

FIG. 2 shows three typical agglutination curves obtained by incubating for 20 minutes standards of $\beta_2$-m with antibody-coated latex diluted 5, 10 or 20 times in the stabilization solution. The best curve was obtained with a dilution rate of 10. The agglutination was read by particle counting with the Technicon ® Autocounter but, as shown in FIG. 3, the estimate of the agglutination can also be performed by turbidimetry with a photometer.

When using the Technicon ® Autocounter equipped with a double threshold system, the assayable range of $\beta_2$-m concentrations can be modified by the setting of the upper threshold. This is due to the fact that a part of the latex aggregates formed during incubation with $\beta_2$-m are of small size. By adjusting the upper threshold so that these small aggregates are eliminated, it was possible to get an assayable range of $\beta_2$-m of 0.25 to 16 μg/l with a detection limit of 0.1 μg/l. Usually, the upper threshold was adjusted to obtain an assayable range of about 1 to 32 μg/l with a detection limit of 0.5 μg/l (FIGS. 2 and 4). This assayable range was similar to that obtained by turbidimetry (FIG. 3).

A postzone phenomenon due to an excess antigen and resulting in an increase of free latex particles was found to occur at a concentration of $\beta_2$-m around 50 mg/l (latex diluted 10 times before assay). As the urines are routinely diluted 10 to 20 times and sera 200 to 400 times, this level corresponds to an initial $\beta_2$-m concentration of 500 to 1000 mg/l in urine and 1000 to 2000 mg/100 ml in serum respectively. In practice, such high levels of $\beta_2$-m in urine or serum have never been observed so that a postzone effect with unknown urine or serum samples is quite unlikely.

Agglutination of antibody-coated latex particles occurred rapidly and was almost complete after 15 minutes. An incubation of 15 minutes is thus sufficient but usually incubation was prolonged for 20 to 30 minutes, the time necessary for pipetting in duplicate a standard curve of $\beta_2$-m with about 20 to 30 unknown samples.

It is not recommended to use a longer incubation time since prolonging the incubation increases the aspecific agglutination and reduces the reproducibility of the results.

Finally, latex particles aggregates formed during incubation with $\beta_2$-m are stable. For instance, the tubes may be stored at least 24 hours at 4° C. before reading, without significant modification of the agglutination.

SPECIFICITY OF THE ASSAY IN URINE AND SERUM

To evaluate whether purified $\beta_2$-m behaves like the native protein and whether other urine or serum components did not interfere with the assay, agglutination curves obtained with serial dilutions (in GBS-BSA buffer) of a serum pool; a urine pool, a serum positive for rhumatoid factor or of purified $\beta_2$-m were compared. FIG. 4 shows that all the curves have the same slope. In the case of serum, a slight interference was however observed at the limit of the assayable range, when the $\beta_2$-m concentration in the solution exceeds 20 μg/l, which corresponds to a dilution lower than 100 times. No attempt was made to prevent this slight interference since in practice such a low dilution rate will never be required. Indeed, due to the sensitivity of the method, the lowest $\beta_2$-m level so far observed in serum (0.08–0.09 mg/100 ml) can still be accurately determined with a sample dilution of 200 to 400 times.

Figure 5:
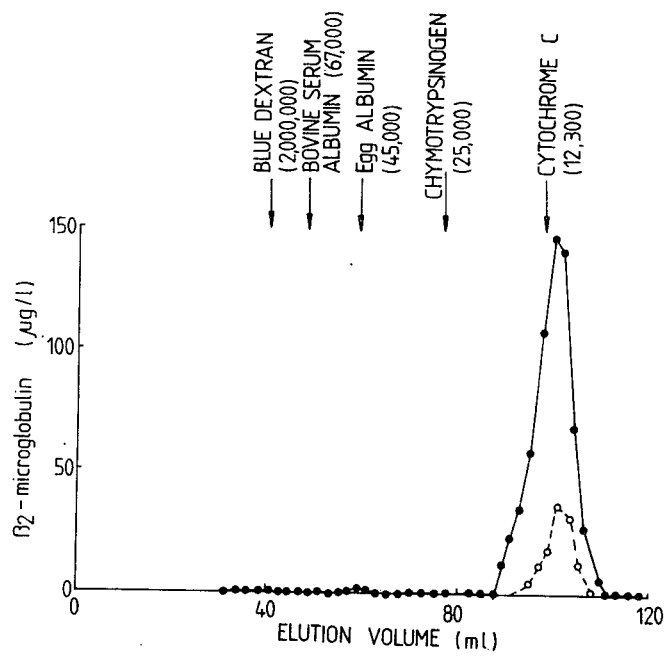
FIG. 5 shows the distribution of $\beta_2$-m in the fractions obtained by chromatography on Sephadex G-75 of a pool of sera (•-•) or urines (o---o).

The similarity of the slopes is again confirmed by the fact that the concentrations of $\beta_2$-m calculated at different dilution rates (n=5) fluctuate in a narrow range: (mean±SD); urine pool: 134±6.2 μg/l; serum pool: 0.164±0.0096 mg/100 ml and serum with rhumatoid factor: 0.168±0.013 mg/100 ml. Finally, chromatography on Sephadex ® G-75 of a urine or serum pool reveals the presence of a single agglutination peak at an elution volume corresponding to the molecular size of $\beta_2$-m (FIG. 5). In the case of serum, a very small peak was also detected at a position corresponding approximately to the molecular weight of HLA (45,000) but this peak represented less than 2 percent of the total amount of $\beta_2$-m present in the serum.

ACCURACY

Purified $\beta_2$-m was added to 10 different urines and sera so that their $\beta_2$-m concentrations were increased by 100 μg/l and 0.4 mg/100 ml respectively. Recovery in urine is on the average 96.6 percent (SE=4.4) with a range of 82.0 to 125 percent. In serum, the mean recovery is 103.9 percent (SE=4.2) and the values range from 83 to 117 percent.

REPRODUCIBILITY

The within assay precision of latex immunoassay was tested by performing 10 determinations of $\beta_2$-m in a urine and serum pool at two different dilutions. As shown in Table 1, all the CV are below 10 percent. The between assay reproducibility was calculated on the basis of 10 different determinations of $\beta_2$-m carried out over one month on the same pool of urines or sera diluted 40 and 200 times respectively. The mean value obtained for urine is 171±17 (SD) μg/l with a CV of 10 percent and that obtained for serum is 0.158±0.0127 (SD) mg/100 ml with a CV of 8.4 percent. In these tests, the main source of variability seems to be the reading by the Autocounter since the CV of 10 successive determinations of $\beta_2$-m concentration from the same assay tube amounts already to 5 percent.

COMPARISON WITH RADIOIMMUNOASSAY

Figure 6:
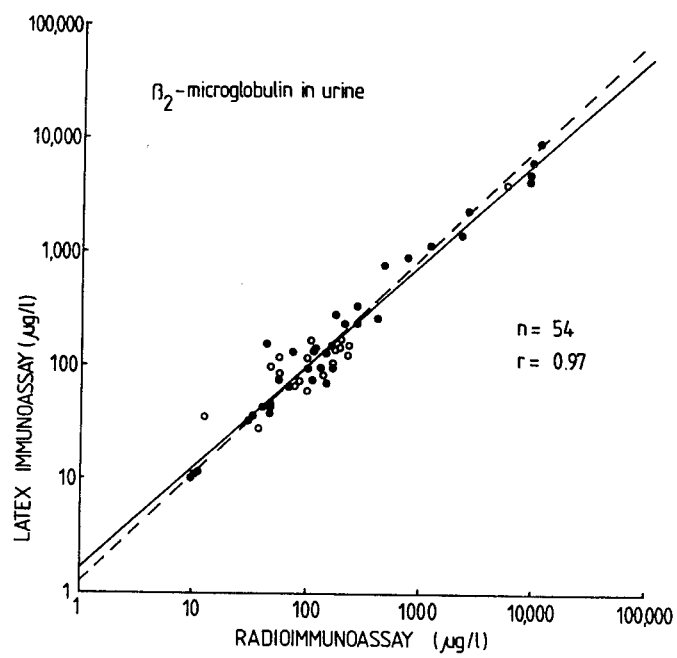
FIG. 6 shows the correlation between $\beta_2$-m concentrations in urine measured by radioimmunoassay (R.I.A.) and latex immunoassay (L.I.A.). The continuous line corresponds to the L.I.A. vs. R.I.A. regression whereas the discontinuous line corresponds to the inverse regression (•): cadmium-exposed worker; (o): control worker.
Figure 7:
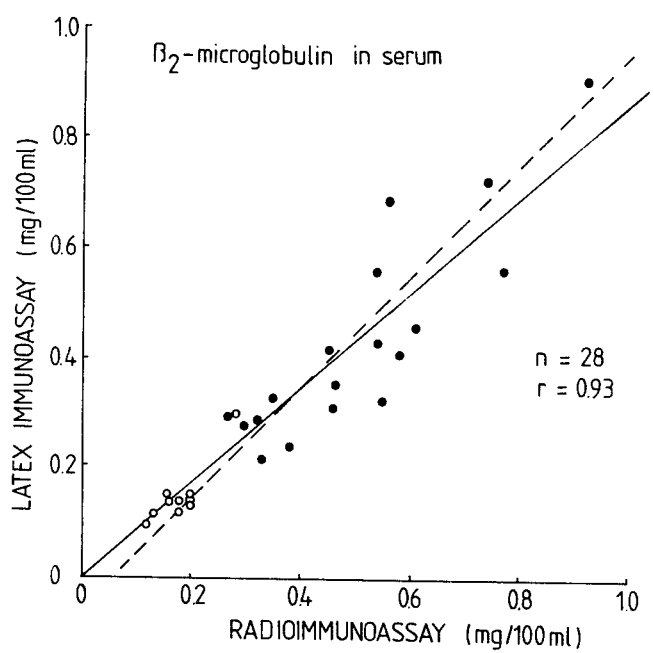
FIG. 7 shows the correlation between $\beta_2$-m concentrations in serum measured by radioimmunoassay (R.I.A.) and latex immunoassay (L.I.A.). Regression lines are represented as in FIG. 5 (•): patients with decreased glomerular filtration rate (o): healthy subjects.

A good correlation was obtained between the latex immunoassay and the radioimmunoassay (Phadebas ®, $\beta_2$-micro-Test) for the termination of $\beta_2$-m in urine (FIG. 6) and serum (FIG. 7). There was no systematic difference between both methods in the high and low concentration range.

VALUES OF $\beta_2$-m IN URINE AND SERUM FROM HEALTHY SUBJECTS

Table 2 summarizes the mean concentrations of $\beta_2$-m in urine and serum in a group of 33 apparently healthy male subjects. These results are in perfect agreement with those found by Evrin and Wibell "The serum levels and urinary excretion of $\beta_2$-microglobulin in apparently healthy subjects," Scand. J. Clin. Lab. Invest. 29, 69–74 (1972).

TABLE I

REPRODUCIBILITY WITHIN ASSAY OF 10 DETERMINATIONS BY LATEX IMMUNOASSAY OF $\beta_2$-m IN A URINE OR SERUM POOL.

| | RATE OF DILUTION | MEAN | SD | CV PERCENT |
|---|---|---|---|---|
| Urine | 1/20 | 416 | 19.0 | 4.56 |
| (μg/l) | 1/40 | 442 | 38.5 | 8.72 |
| Serum | 1/200 | 0.210 | 0.016 | 7.80 |
| (mg/100 ml) | 1/400 | 0.202 | 0.015 | 7.46 |

TABLE II $\beta_2$-m CONCENTRATIONS DETERMINED BY LATEX IMMUNOASSAY SERUM AND URINE OF 33 HEALTHY MALE SUBJECTS.

| | Age (years) | | | | | |
|---|---|---|---|---|---|---|
| | 20–45 17 | | | 46–67 16 | | |
| | MEAN | SD | RANGE | MEAN | SD | RANGE |
| $\beta_2$-m in serum mg/100 ml. | 0.149 | 0.023 | 0.104–0.186 | 0.158 | 0.037 | 0.13–0.20 |
| $\beta_2$-m in urine | | | | | | |
| μg/l | 68.5 | 36.2 | 11.4–143 | 106.2 | 87.1 | 27.9–374 |
| μg/g creatinine | 45.0 | 28.6 | 8.4–119 | 63.8 | 47.1 | 18–209 |

We claim:

1. A method for determining $\beta_2$-microglobulin concentration in a human urine or serum sample comprising the steps of:
   (a) coating latex particles with an antibody against the $\beta_2$-microglobulin;
   (b) incubating the antibody-coated particles diluted in a stabilizing solution with the sample so as to permit the $\beta_2$-microglobulin to agglutinate a proportion of the particles, said proportion being related to the concentration of $\beta_2$-microglobulin in the sample; and
   (c) quantitating the unagglutinated particles and thereby determining the $\beta_2$-microglobulin concentration in the sample.

2. A method according to claim 1, wherein the stabilizing solution consists of glycine buffered saline containing bovine serum albumin.

3. A method according to claim 2, wherein said stabilizing solution is adjusted to about pH 10.

4. A method according to claim 1 or 2 wherein the latex particles are coated with antibody against the $\beta_2$-microglobulin by the following steps:
   (a) diluting the antibody with glycine buffered saline;
   (b) adding the latex particles to the diluted antibody with agitation; and
   (c) precipitating the latex particles followed by the redispersement of the latex particles in glycine buffered saline;

the resulting antibody-coated latex particles being suitable for long-term storage.

* * * * *